(12) United States Patent
Wagner

(10) Patent No.: US 6,352,545 B1
(45) Date of Patent: Mar. 5, 2002

(54) BREATH SYSTEM APPLIANCE WITH DORSAL APPLICATOR AND SCRAPER

(76) Inventor: Eugene C. Wagner, c/o Dental Concepts LLC 100 Clearbrook Rd., Elmsford, NY (US) 10523

( * ) Notice: Subject to any disclaimer, the term of this patent is extended or adjusted under 35 U.S.C. 154(b) by 0 days.

(21) Appl. No.: 09/422,313

(22) Filed: Oct. 21, 1999

Related U.S. Application Data

(63) Continuation-in-part of application No. 09/307,705, filed on May 10, 1999, now Pat. No. 6,083,235.

(51) Int. Cl.[7] ............................................. A61B 17/24
(52) U.S. Cl. ........................................ 606/161; 15/111
(58) Field of Search ................... 606/1, 160, 161; 600/56; 604/77; 424/435, 439; D24/101, 135, 136; D1/105; 15/110, 111, 114

(56) References Cited

U.S. PATENT DOCUMENTS 2,218,072 A * 10/1940 Runnels ...................... 606/161
2,491,274 A * 12/1949 McNeill ...................... 606/161
3,943,928 A * 3/1976 Lariccia et al.
5,085,634 A * 2/1992 Lackney
5,176,151 A * 1/1993 Harding
5,735,864 A * 4/1998 Heisinger, Jr. ............... 606/161
6,004,334 A * 12/1999 Mythen ....................... 606/161
6,083,235 A * 7/2000 Wagner ....................... 606/161

* cited by examiner

Primary Examiner—Henry J. Recla
Assistant Examiner—William W. Lewis
(74) Attorney, Agent, or Firm—Natter & Natter

(57) ABSTRACT

A breath system appliance includes a planar thin elongate body having an applicator head at one end and a scraper head at the other end. The applicator head carries a troche having an oral hygiene and/or breath freshening active constituent. The active constituent may include an antibacterial agent, an antiseptic agent, a flavoring agent, an oxidizing agent and an anesthetizing agent. The active constituent is applied as a coating to dorsal surfaces of a user. The scraper head is applied against dorsal surfaces of the user to dislodge food debris and other odor generating matter from the dorsum of the user after application of the troche, before application of the troche, or both before and after. The appliance may be packaged in a sealed packet.

18 Claims, 3 Drawing Sheets

BREATH SYSTEM APPLIANCE WITH DORSAL APPLICATOR AND SCRAPER

RELATED APPLICATION

This is a continuation-in-part of Application Ser. No. 09/307,705 filed May 10, 1999, now U.S. Pat. No. 6,083,235 entitled BREATH SYSTEM APPLIANCE WITH DORSAL APPLICATOR AND SCRAPER.

BACKGROUND OF THE INVENTION

1. Field of the Invention

The present invention relates generally to oral hygiene appliances and more specifically to devices which promote oral hygiene by removing debris from one's tongue.

2. Antecedents of the Invention

The general public has been highly conscious of oral hygiene, not only from a social standpoint, but additionally in its relationship to overall health. While basic oral hygiene devices such as toothbrushes, toothpaste, tooth powder, interdental stimulators, interproximal brushes, dental floss, toothpicks and dental picks, e.g. U.S. Pat. No. 4,326,548, have been in use through the years, in recent years there has been a proliferation of do-it-yourself oral hygiene cosmetic products, including various tooth whitening preparations, e.g. U.S. Pat. No. 5,084,268 as well as tooth polishers, for improvement of the appearance of one's mouth.

The public has also been cognizant of the need to combat mouth malodor in daily social encounters. Various factors have been attributed to the generation of oral malodor including improper brushing, failure to brush and/or failure to floss. Other factors include the presence of various compounds in the oral cavity which are alleged to cause malodor, such as hydrogen sulfide.

It has also been recognized that minute food particles and debris as well as odor producing bacteria resided on the tongue, particularly on the dorsal (upper) surface thereof, i.e. the dorsum.

The dorsum has been characterized as a rough surface which is covered with papillae. The anterior of the dorsum is covered with fungiform papillae and the posterior (pharyngeal) surface is covered with fungiform papillae interspersed with filiform papillae.

Food particles and the breakdown products of foods became lodged in crevices between the papillae. Dense bacterial populations and the many bacterial species resident on the dorsum have been known to colonize. It is believed that the dorsum is the source of most of the bacteria in the oral cavity and the source of oral malodor.

The prevalent use of mouthwashes, breath mints and breath sprays did not alleviate or reduce the source of malodor, but merely served to mask the condition.

Various tongue scrapers such as those disclosed in the patents to Heisinger (U.S. Pat. No. 5,735,864), Andrews (U.S. Pat. No. 4,079,478), Nack (U.S. Pat. No. 5,226,179) and Bhaskar (U.S. Pat. No. 3,943,592) are among the devices which have been suggested for cleaning the tongue to remove food debris and other material accumulated on the dorsum.

Although such devices were capable of scraping the dorsum and loosening debris accumulated thereon, absent was the ability to adequately scrape the pharyngeal tissue surface due to the tendency of any scraping appliance to induce a gag reflex. Additionally, treatment of existing malodor conditions required the employment of a mouthwash or other breath freshener since tongue scrapers provided primarily prophylactic, rather than immediate relief.

Further, none of the prior devices gained a measure consumer acceptance, either because they were too difficult to use, to costly to manufacture, or were otherwise unsuited for general use.

SUMMARY OF THE INVENTION

A breath system appliance with a dorsal troche applicator and a scraper includes a generally flat, relatively thin, elongate body. Projecting transversely from the longitudinal axis of the body at one end thereof is a generally planar, relatively thin troche applicator head while a scraper head projects transversely from the other end of the body.

Adhered to a face of the applicator head is a thin troche having oral hygiene and/or breath freshening active constituents. The troche is applied by rubbing over dorsal surfaces whereby the active constituents are released when the troche dissolves in saliva.

The troche may be applied to the dorsal surfaces either before or after scraping the dorsal surfaces with an array of ribs and/or teeth which project from the scraper head.

The lower face of the scraper head includes the ribs, while the opposite face carries a peripheral array of teeth.

From the foregoing compendium, it will be appreciated that it is an aspect of the present invention to provide a breath system appliance of the general character described which is not subject to the disadvantages of the antecedents of the invention aforementioned.

A feature of the present invention is to provide a breath system appliance of the general character described which is well suited to promote overall oral hygiene and to reduce the rate of plaque formation in the oral cavity.

A further aspect of the present invention is to provide a breath system appliance of the general character described which is simple to use.

Another further feature of the present invention is to provide a self-contained oral hygiene appliance of the general character described which is well suited to effectively dislodge debris from surfaces of the dorsum.

To provide a breath system appliance of the general character described which reduces the tendency of a user to gag is a still further aspect of the present invention.

Another consideration of the present invention is to provide a breath system appliance of the general character described which is portable and well suited for carrying about one's person for routine usage away from home.

Yet another feature of the present invention is to provide a breath system appliance of the general character described which is disposable and thus well suited for one time usage by hotel guests, at health spas, and the like.

It is a further aspect of the present invention is to provide a breath system appliance of the general character described which is relatively low in cost and well suited for economic mass production fabrication.

Yet another consideration of the present invention is to provide a breath system appliance of the general character described wherein dorsal surfaces are coated with a breath freshening and/or oral hygiene medium for effective removal of food debris, bacteria and other risk factors associated with oral odor as well as for providing immediate alleviation of oral malodor.

Yet another aspect of the present invention is to provide a breath system appliance of the general character described which is well suited to utilize any of a number of active constituents or combinations thereof for efficacious treatment of oral malodor.

An additional feature of the present invention is to provide a breath system appliance of the general character described which is capable of dispensing a coating of active constituents over dorsal surfaces for enhanced freshening of dorsal surfaces.

A still further consideration of the present invention is to provide a breath system appliance of the general character described which is highly efficacious for both immediate and long term alleviation of oral malodor.

Other aspects, features and considerations of the present invention in part will be obvious and in part will be pointed out hereinafter.

With these ends in view, the invention finds embodiment and certain combinations of elements, arrangements of parts and series of steps by which the aforesaid aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings in which is shown one of the various possible exemplary embodiments of the invention.

DESCRIPTION OF THE PREFERRED EMBODIMENTS

Figure 1:
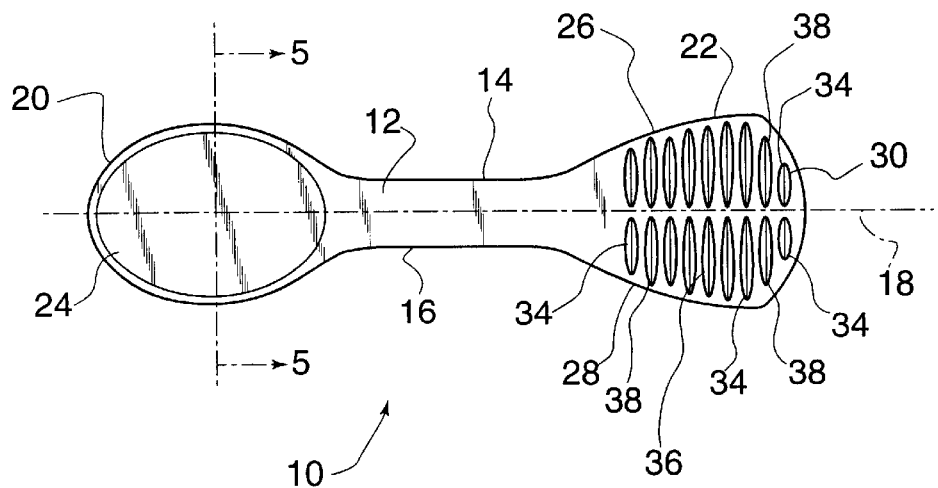
FIG. 1 is a bottom view of a breath system appliance constructed in accordance with and embodying the invention and showing an elongate planar body having at one end, an enlarged troche applicator head with a troche fixed to its lower face and at the other end of the body, an enlarged scraper head with an array of ribs projecting downwardly.
Figure 2:
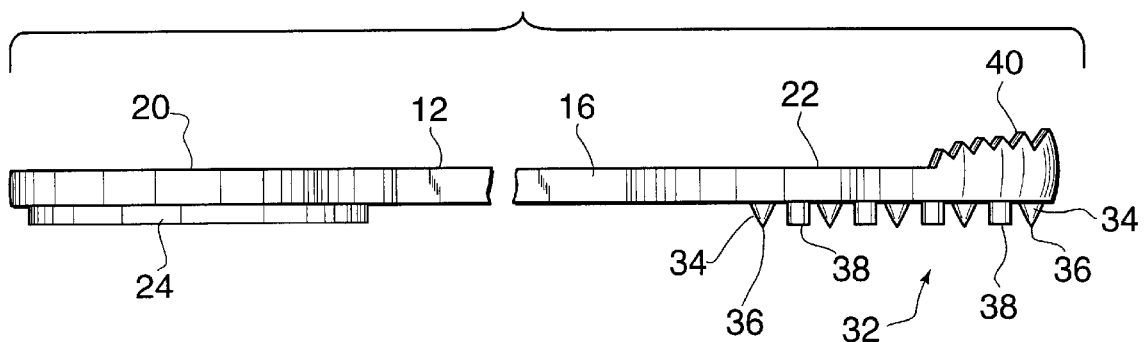
FIG. 2 is an enlarged scale side elevational view of the appliance and showing a plurality of teeth projecting from the upper face of the scraper head adjacent the periphery thereof.

Referring now in detail to the drawings, the reference numeral 10 denotes generally a breath system appliance constructed in accordance with and embodying the invention. The appliance comprises a generally flat relatively thin elongate body 12 having a pair of longitudinal side edges 14, 16 substantially parallel to a longitudinal axis, 18. Projecting transversely from the axis 18 at one end of the body 12 is an enlarged elliptical troche applicator head 20. At the opposite end of the body 12 is an enlarged paddle shaped scraper head 22 which also extends transversely from the longitudinal axis 18.

Adhered to the lower face of the applicator head 20 is a troche 24. In accordance with the invention, the troche 24 is formed with one or more active constituents having breath freshening and/or oral hygiene characteristics including anesthetic, antiseptic and astringent characteristics. Ansthetising properties are particularly beneficial if the troche 24 is applied prior to scraping dorsal surfaces in order to retard a gag reflex.

Among active constituents are antibacterial agents, antiseptic agents, plaque inhibiting agents and flavoring agents. Typical constituents include thymol, eucalyptus oil, zinc chloride, menthol, microencapsulated peroxides and/or stabilized chlorine dioxide and polydimethylsiloxane-poloxamer 407.

While the troche 24 maybe formulated in accordance with traditional techniques, e.g. *The Dispensatory of the United States of America*, 24th Edition, 1947 J. B. Lippencott Co., Page 1243, incorporated herein by reference, one or more of the active constituents may be incorporated in a hard candy or mint for example, with or without a center envelope 27 which encapsulates one or more active constituents in liquid form. The term "troche" should be interpreted as including not only troches in the conventional sense but also lozenges, pastilles, hard candies as well as semi soft candies, mints and the like.

Figure 5:
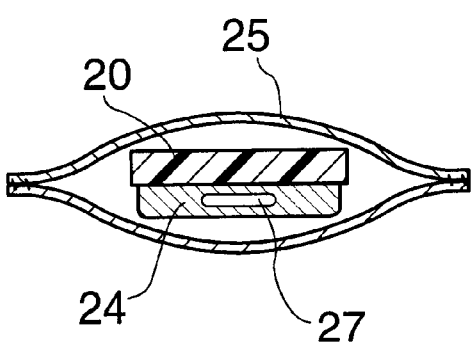
FIG. 5 is an enlarged sectional view through the appliance, the same being taken along line 5—5 of FIG. 1 and through a packet in which the appliance is wrapped.

As illustrated in FIG. 5, the appliance may be individually wrapped in a sealed packet 25 for ease in carrying in one's pocket for example without the danger of contaminant contact.

The troche 24 is applied to dorsal surfaces by rubbing over the surfaces, whereby the troche is dissolved in saliva and the active constituents are released to coat the dorsal surfaces. Such troche application may take place either before or after scraping dorsal surfaces with the scraper head 22 or both before and after scraping.

To apply the troche, the appliance 10 is grasped at the mid-portion of the body 12 and the applicator head 20 is inserted into the oral cavity with the troche 24 facing the user's tongue. The troche 24 is pressed against and moved across the dorsal surfaces of the user's tongue with saliva dissolving the troche to release a coating of active constituents over surfaces of the dorsum.

After the dorsum has been coated with the active constituents, the applicator head 20 is removed from the oral cavity and the scraper head 22, at the opposite end of the body 12, is inserted.

It should be noted that the scraper head 22 differs from the applicator head 20. In lieu of having an elliptical plan configuration, the scraper head 22 has a generally paddle shaped configuration with a pair of diverging side edges 26, 28. A curved end surface 30, having a radius of curvature significantly larger than the radius of curvature of the end of the applicator head 20 is also found on the scraper head 22.

Figure 3:
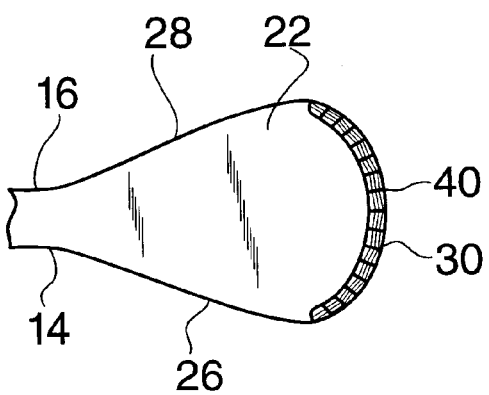
FIG. 3 is a fragmentary top plan view showing the peripheral teeth.
Figure 4:
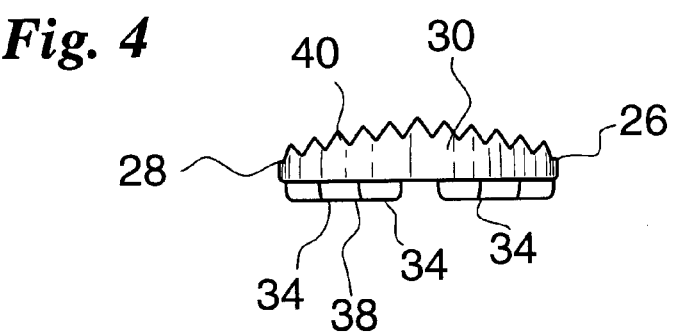
FIG. 4 is an enlarged scale right end view of the appliance showing the peripheral teeth projecting upwardly and the ribs projecting downwardly from opposite faces of the scraper head.

Symmetrically positioned along a lower face of the scraper head 22 is an array 32 of ribs 34, 38. As will be noted from an examination of FIG. 3, the array 32 is symmetric about the longitudinal axis 18. The array 32 includes rows of downwardly projecting transverse ribs 34, 38 with alternate ribs 34 having a relatively keen scraping edge 36 and with adjacent ribs 38 having terminal surfaces which are blunt.

It should be noted that alternating rows of keen and blunted edge ribs are but one of any number of rib configurations suitable for employment in the invention. All ribs could have blunted or keen edges and various combinations in between. Further, the array pattern, as well as the number of ribs may be varied without departing from the invention.

On the opposite or upper face of the scraper head 22 is a peripheral array of teeth 40.

In use, after the dorsum has been coated with the troche active constituents, the scraper head 22 is inserted into the oral cavity and either the array 32 of ribs 34, 38 on the lower face or the array of teeth 40 on the upper face are wiped against the dorsum in a back and forth, circular, oval or irregular scraping pattern.

The appliance 10 is then rotated about its axis 18 so that the opposite face of the scraper head 22 engages the dorsum and the wiping procedure is repeated.

It should be appreciated that the entire breath system appliance 10 can be suitably molded of one piece construction, with the exception of the troche 24, from any of a number of known thermoplastics which are suited for use within the oral cavity including, but not limited to, polyethylene, polypropylene, acetals, polycarbonates, acrylonitrile-butanine-styrene, etc.

By way of example and not limitation, the appliance body 12 has length in the range of approximately 3 inches (75 mm.) to 4 inches (100 mm.) and preferably 3½ inches (90 mm.). The applicator and scraper heads may be dimensioned with a maximum transverse width in the order of ⅝ to ⅞ inches (16 to 23 mm.) and the thickness of the body 12 may range between 1 to 2 mm.

Figure 6:
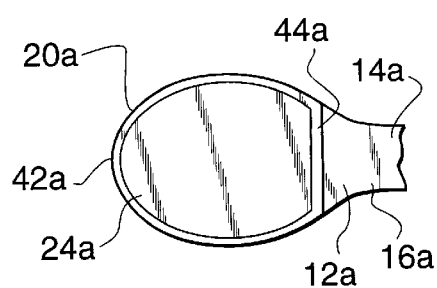
FIG. 6 is a fragmentary bottom view of an alternate embodiment wherein a troche is carried within a peripheral wall.
Figure 7:
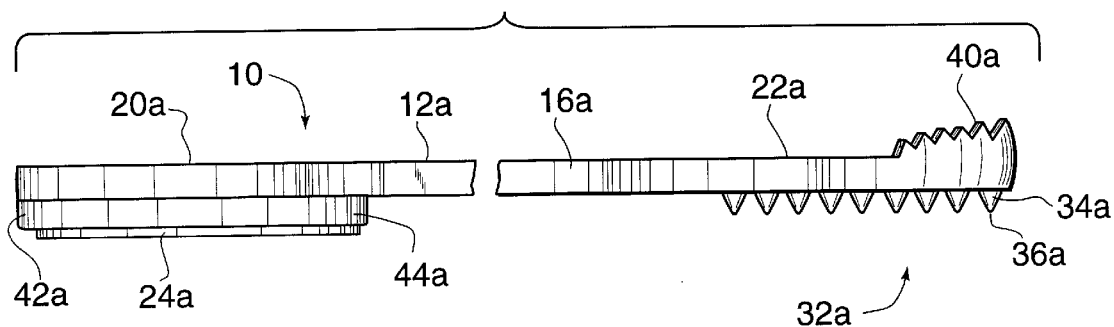
FIG. 7 is an enlarged scale side elevational view of the alternate embodiment showing the peripheral wall and an alternate array of ribs.

In FIGS. 6 and 7, there is illustrated an alternate embodiment of the invention wherein like numerals have been employed to denote like components of the previous embodiment, however, bearing the suffix "a". The alternate embodiment differs from the embodiment previously described in that a troche is circumscribed by a peripheral wall and further in that an array of ribs includes ribs with substantially uniform transverse cross section.

Referring now in detail to FIGS. 6 and 7, it will be seen that an appliance 10a includes a thin elongate body 12a having a pair of substantially parallel longitudinal side edges 14a, 16a. At one end of the body 12a, there is an elliptical applicator head 20a which carries a troche 24a within a peripheral wall 42a. The wall 42a is substantially elliptical except for a truncation end wall 44a transverse to the longitudinal axis of the ellipse.

As seen from an examination of FIG. 7, the height of the peripheral wall 42a is slightly less than the thickness of the troche 24a such that a surface of the troche 42a is exposed for contact against the user's dorsal surfaces.

It should also be noted that the body 12a includes, at its opposite end, a scraper head 22a having a peripheral array of teeth 40a projecting from one face thereof and, projecting from the opposite face an array 32a of ribs 34a, each having a uniform transverse cross section with a longitudinal edge 36a. The edge 36a is slightly rounded, e.g. having a radius of 0.2 mm.

In all other aspects, the appliance 10a of the alternate embodiment is identical to that of the embodiment previously disclosed.

It should be understood that the troche active constituent serves manifold functions; one of its purposes is to provide a source of immediate breath freshening which benefit is derived from its flavoring constituents. It additionally serves to destroy odor causing bacteria and sulphites by conjunctive action of antiseptic and oxidizing agents. Further, the employment of anesthetizing agents is beneficial in reducing the gag reflex which may be encountered when the applicator and scraper heads approach and contact the pharyngeal surfaces of the dorsum. Gag reflex is also significantly reduced due to the overall low profile of the appliance.

A further significant function of the troche active constituents is to facilitate the dislodgement and removal of food and other debris which has accumulated on dorsal surfaces between the papillae. The active constituent thus enhances the efficacious results to be achieved through implementation of the scraper head.

Thus it will be seen that there is provided a breath system appliance which achieves the various aspects, features and considerations of the present invention and which is well-suited to meet the conditions of practical usage.

Since various possible embodiments might be made of the present invention and since various changes might be made in the exemplary embodiment shown herein without departing from the spirit of invention, it should be understood that all matter herein described or shown in the accompanying drawings should be interpreted as illustrative and not in a limiting sense.

Having thus described the invention, there is claimed as new and desired to be secured by Letters Patent:

1. An appliance for alleviation of oral malodor, the appliance comprising a generally planar thin elongate body, an applicator head at one end of the body and a dorsal scraper head at the other end of the body, the applicator head including a troche carrying an active constituent, the active constituent being released from the troche and applied as a coating to the dorsal surfaces of a user, the dorsal scraper head including at least one scraping element for scraping dorsal surfaces of the user, the scraping element projecting outwardly from the planar body.

2. An appliance for alleviation of oral malodor as constructed in accordance with claim 1 including a plurality of scraping elements comprising ribs.

3. An appliance for alleviation of oral malodor as constructed in accordance with claim 2 wherein the ribs include relatively keen scraping edges, whereby effective dislodgement of debris carried on dorsal surfaces is achieved.

4. An appliance for alleviation of oral malodor as constructed in accordance with claim 3 wherein selected ribs include keen edges and selected ribs include blunt edges.

5. An appliance for alleviation of oral malodor as constructed in accordance with claim 4 wherein alternate ribs are provided with keen edges and ribs adjacent the alternate ribs are provided with blunt edges.

6. An appliance for alleviation of oral malodor as constructed in accordance with claim 5 wherein the teeth are positioned adjacent a peripheral edge of the dorsal scraper head.

7. An appliance for alleviation of oral malodor as constructed in accordance with claim 2 wherein the ribs include blunt edges.

8. An appliance for alleviation of oral malodor as constructed in accordance with claim 2 including a plurality of scraping elements comprising teeth.

9. An appliance for alleviation of oral malodor as constructed in accordance with claim 1 wherein the active constituent is carried in a liquid center of the troche.

10. An appliance for alleviation of oral malodor as constructed in accordance with claim 1 wherein the active constituent comprises an antiseptic.

11. An appliance for alleviation of oral malodor as constructed in accordance with claim 1 wherein the active constituent comprises an anesthetic.

12. An appliance for alleviation of oral malodor as constructed in accordance with claim 1 wherein the active constituent is selected from the group consisting of zinc chloride, thymol, eucalyptus oil, menthol, peroxides and chlorine dioxide.

13. An appliance for alleviation of oral malodor as constructed in accordance with claim 1 wherein the active constituent is in dry form, the active constituent being activated by a liquid.

14. An appliance for alleviation of oral malodor as constructed in accordance with claim 13 wherein the liquid comprises saliva.

15. A treatment for alleviation of oral malodor in a person, the treatment comprising:
   a) providing a troche secured to a thin elongate body, the troche carrying an active constituent selected from the group consisting of zinc chloride, thymol, eucalyptus oil, menthol, peroxides and chlorine dioxide,
   b) inserting the troche in the person's mouth while grasping the thin elongate body in the person's hand,
   c) coating the dorsal surfaces of the person's tongue with the active constituent by placing the troche in contact with the dorsal surfaces, and
   d) thereafter scraping the coated dorsal surfaces.

16. A treatment for alleviation of oral malodor in accordance with claim 15 wherein the thin elongate body includes a scraper and step d) is performed utilizing the scraper.

17. A treatment for alleviation of oral malodor in a person, the treatment comprising:
   a) providing a troche secured to a thin elongate body, the troche carrying an active constituent selected from the group consisting of zinc chloride, thymol, eucalyptus oil, menthol, peroxides and chlorine dioxide,
   b) scraping the dorsal surfaces of the person's tongue,
   c) thereafter inserting the troche in the person's mouth while grasping the thin elongate body in the person's hand, and
   d) coating the dorsal surfaces of the person's tongue with the active constituent by placing the troche in contact with the dorsal surfaces.

18. A treatment for alleviation of oral malodor in accordance with claim 17 wherein the thin elongate body includes a scraper and step b) is performed utilizing the scraper.

* * * * *